United States Patent [19]

Borden et al.

[11] Patent Number: 5,406,830

[45] Date of Patent: Apr. 18, 1995

[54] PARTICLE MONITOR FOR LOADLOCK SOFT PUMP LINES

[75] Inventors: Peter G. Borden, San Mateo; Martin D. Elzingre, Campbell, both of Calif.

[73] Assignee: High Yield Technology, Sunnyvale, Calif.

[21] Appl. No.: 62,655

[22] Filed: May 14, 1993

[51] Int. Cl.$^6$ .................................... G01N 33/00
[52] U.S. Cl. ......................................... 73/28.01
[58] Field of Search ............... 73/28.01, 28.04, 863.23

[56] References Cited

U.S. PATENT DOCUMENTS

| 4,797,054 | 1/1989 | Arii | 414/217 |
|---|---|---|---|
| 5,031,674 | 7/1991 | Mack | 141/66 |
| 5,083,865 | 1/1992 | Kinney et al. | 356/338 |
| 5,271,264 | 12/1993 | Chanayem | 73/28.01 |

Primary Examiner—Hezron E. Williams
Assistant Examiner—Michael J. Brock
Attorney, Agent, or Firm—Skjerven, Morrill, MacPherson, Franklin & Friel

[57] ABSTRACT

An apparatus and a method provide a particle monitor mounted in an exhaust line of a loadlock chamber. The apparatus of the present invention comprises a particle monitor and a particle filter mounted down stream from the particle monitor away from the loadlock chamber. In one embodiment, the particle filter can be implemented by a wire-mesh screen, or a perforated stainless steel screen. The particle filter can be mounted in a centering ring of a standard vacuum connection which comprises two flanges, a centering ring, and an O-ring held together by a clamp.

12 Claims, 2 Drawing Sheets

PARTICLE MONITOR FOR LOADLOCK SOFT PUMP LINES

BACKGROUND OF THE INVENTION

1. Field of the Invention

The present invention relates to the use of particle monitors in a manufacturing process; and, in particular relates to the relocation of a particle filter in a loadlock chamber to accommodate particle level monitoring by a particle sensor.

2. Discussion of the Related Art

In most vacuum process equipment for semiconductor manufacturing, a loadlock is used to introduce silicon wafers from outside the equipment to the process chamber. A typical configuration is shown in FIG. 1. As shown in FIG. 1, the semiconductor wafers to be processed are brought to the process equipment 100 in a cassette 101. The loadlock chamber 102 is then vented to atmospheric pressure, and one or more wafers brought into loadlock chamber 102. Loadlock chamber 102 is then pumped down to a vacuum pressure used in the manufacturing process, and the wafers in loadlock chamber 102 are then transferred to process chamber 103.

One significant problem with the configuration of FIG. 1 is that, during the pumping process to reduce the pressure of the loadlock chamber, particles are stirred up. Many of these particles land on the wafers in loadlock chamber 102, leading to wafer contamination, while other particles are drawn into pump line 105. Since the number of particles landing on the wafer and the number of particles flowing out the pump line are both proportional to the number of particles stirred up, a direct relationship exists between the severity of wafer contamination and the count of particles in the pump line. Thus, a particle monitor measuring the particle level in the exhaust line 105 carrying gas out of the loadlock chamber 102 can provide an indication of wafer contamination in loadlock chamber 102.

In many systems, however, measurement of the particle level in the pump line 105 cannot be easily performed. This is because a particle filter 106 is installed in pump line 105 at the opening of pump line 105 into loadlock chamber 102. Particle filter 106 prevents particles such as silicon chips from being drawn onto the sealing surface of a vacuum valve located downstream in pump line 105.

SUMMARY OF THE INVENTION

In accordance with the present invention, an apparatus and a method provide a particle monitor mounted in an exhaust line of a loadlock chamber. The apparatus of the present invention comprises a particle monitor and a particle filter mounted in the exhaust line downstream from the particle monitor away from the loadlock chamber.

In one embodiment of the present invention, the particle filter is implemented by either a wire-mesh screen, or a perforated stainless steel screen. The particle filter is mounted in a centering ring of a standard vacuum connection which comprises two flanges, a centering ring, and an O-ring held together by a clamp. This vacuum connection allows easy access to the particle filter for purposes such as cleaning.

The particle filter slows down the gas flow at the particle monitor, so as to allow higher detection performance. By adjusting the mesh size in the particle filter, a desired pumping speed at the loadlock chamber can be achieved.

DETAILED DESCRIPTION OF THE PREFERRED EMBODIMENTS

Figure 2A:
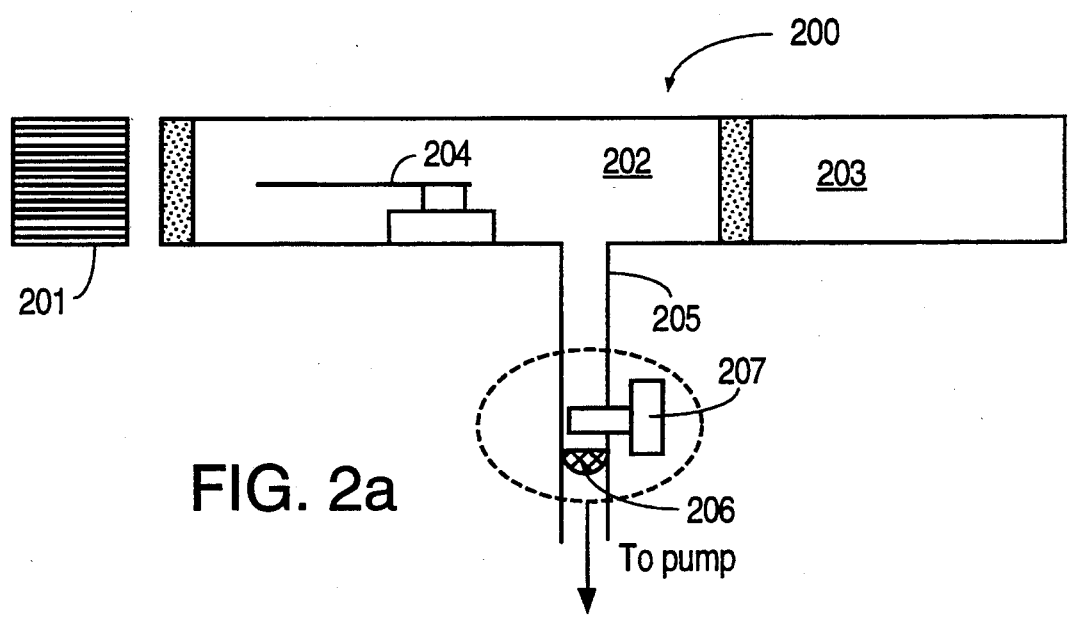
FIG. 2a shows a loadlock chamber 202 having a particle monitor 207 and a particle filter 206, in accordance with the present invention.

The present invention allows installation of both a particle monitor and a particle filter in the exhaust line emerging from a loadlock chamber. An embodiment of the present invention is shown in FIG. 2a, where vacuum processing equipment 200 includes particle monitor 207 and particle filter 206. Loadlock chamber 202 and process chamber 203 are substantially identical to loadlock chamber 102 and process chamber 103.

Figure 1:
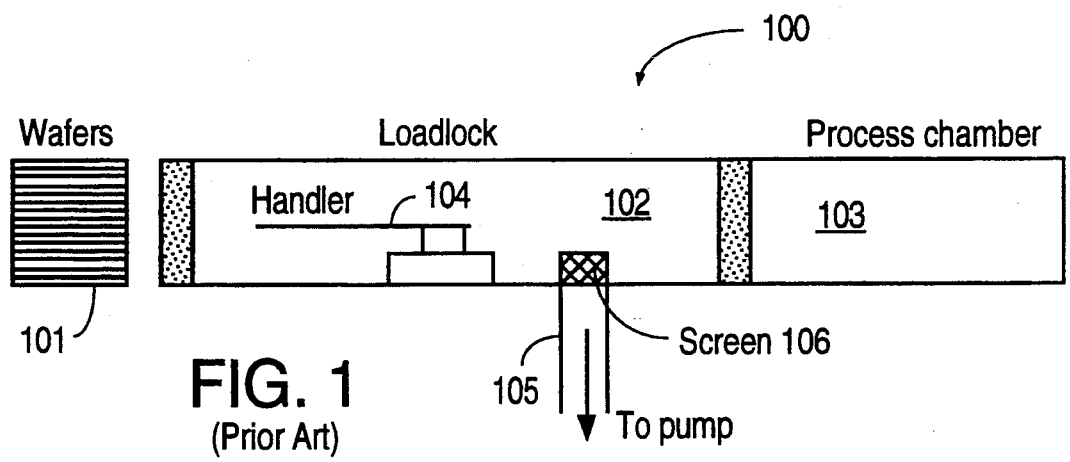
FIG. 1 shows a conventional loadlock chamber 102 for introducing silicon wafers into a process chamber 103.
Figure 3B:
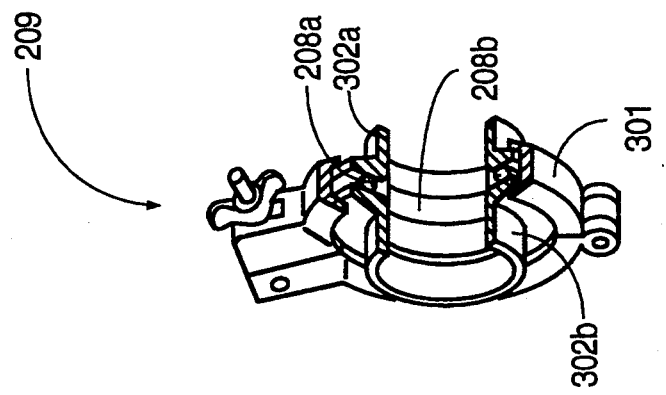
FIG. 3b shows a sectional view of vacuum connection assembly 209 of FIG. 3a held together by a clamp ring 301; the sectional view shows flanges 302a and 302b and center ring assembly 208 in their functional positions held together by clamp ring 301.
Figure 3A:
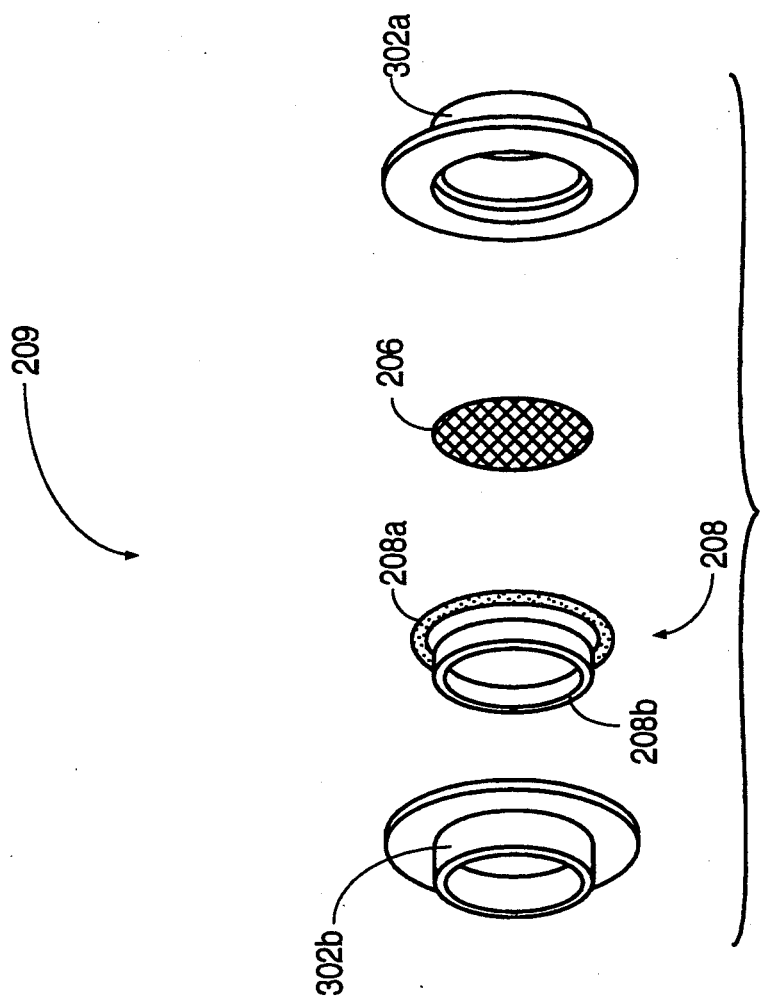
FIG. 3a shows the components of vacuum connection assembly 209, including two flanges 302a and 302b, particle filter 206 and a centering assembly 208, which includes centering 209a and O-ring 209b; vacuum connection assembly 209 is held tightly together by a clamp ring 301 shown in FIG. 3b.

In accordance with the present invention, the conventional particle filter, such as particle filter 106 shown in FIG. 1, is eliminated from the normal location near the opening of pump line 205 into loadlock chamber 202. With the conventional particle filter removed, particle sensor 207 can be mounted in pump line 205. Particle sensor 207 is provided in a housing 211, which has two openings having the same cross section as pump line 205. Thus, housing 211 can be spliced into pump line 205 using standard vacuum connections. FIG. 3a shows a vacuum connection assembly 209, which includes an O-ring seal between two flange faces 302a and 302b, with the O-ring 208a being held in place by a centering ring 208b. The assembly of the flanges, the O-ring and the center ring are held tightly together by a clamp ring 301 (FIG. 3b). In order to mount particle sensor 207, two such assemblies, assemblies 209 and 210, are provided on each side of housing 211.

Figure 2B:
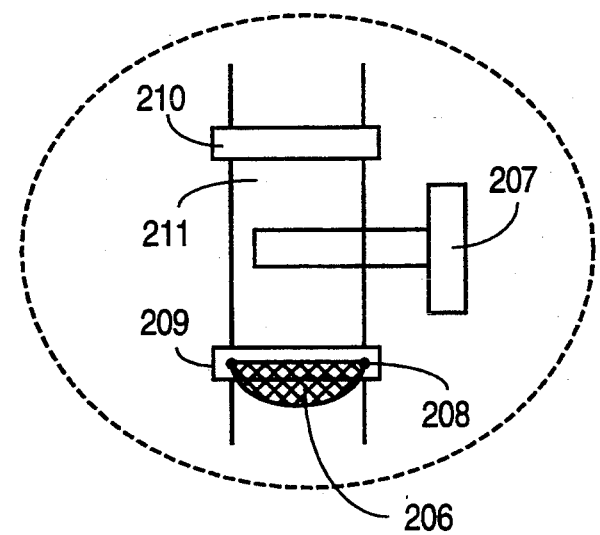
FIG. 2b shows in further detail the assembly including particle monitor 207 and particle filter 206 of FIG. 2a, in accordance with the present invention.

The present invention provides for filtering of particles by a particle filter 206 (see FIG. 3a, where particle filter 206 is shown in the operational position suggested in FIG. 2b), which is mounted in pump line 205 on the pump side of particle sensor 207. Particle filter 206, which is preferably a wire mesh or a thin stainless steel foil with perforated holes, need not be taut, so as to allow its surface area to be adjusted to achieve the desired pumping speed at loadlock chamber 202. Particle filter 206 is held by the centering ring 208b of assembly 209. The pumping speed at loadlock chamber 202 can be adjusted by increasing or decreasing the mesh size of particle filter 206.

An additional advantage of the present invention is that the effective pumping speed at particle sensor 207 is reduced by the impedance of particle filter 206. Thus, particles carried in the exhaust gas flow through particle sensor 206 at a slower speed, and consequently are more easily detected. Since particle filter 206 can be easily removed by unlocking the clamp ring, easy access to particle filter 206 for such purpose as cleaning is achieved without entry to loadlock chamber 202.

The detailed description above is provided to illustrate the specific embodiments of the present invention and is not intended to be limiting of the present invention. Numerous modifications and variations within the scope of the present invention is possible. The present invention is defined by the following claims.

We claim:

1. An apparatus for monitoring a particle level of a loadlock chamber mounted in a pump line connected to said loadlock chamber, said apparatus comprising:
   a particle sensor mounted in said pump line; and
   a particle filter mounted in said pump line on the side of said particle sensor away from said loadlock chamber, wherein said particle filter is mounted in a centering ring between two flanges.

2. An apparatus as in claim 1, wherein said particle filter comprises a wire-mesh screen.

3. An apparatus as in claim 1, wherein said particle filter comprises a perforated stainless steel screen.

4. An apparatus as in claim 1, wherein said particle sensor has a housing having first and second ends, said first and second ends being spliced into said pump line using first and second means of vacuum connection.

5. An apparatus as in claim 4, wherein each of said first and second means of vacuum connection comprises:
   first and second flanges;
   a centering ring between said first and second flanges;
   an O-ring mounted on said centering ring; and
   a clamp holding said centering ring and said first and second flanges tightly together, such that said O-ring effectuates a vacuum seal at said vacuum connection.

6. An apparatus as in claim 5, wherein said particle filter is mounted in the one of said first and second means of vacuum connections which is located further from said loadlock chamber.

7. A method for monitoring a particle level of a loadlock chamber mounted in a pump line connected to said loadlock chamber, said method comprising the steps of:
   providing a particle sensor mounted in said pump line; and
   providing a particle filter mounted in said pump line on the side of said particle sensor away from said loadlock chamber, wherein said particle filter is mounted in a centering ring between two flanges.

8. A method as in claim 7, wherein said step of providing a particle filter provides a wire-mesh screen.

9. A method as in claim 7, wherein said step of providing a particle filter provides a perforated stainless steel screen.

10. A method as in claim 7, wherein said step of providing a particle sensor provides a housing for said particle sensor having first and second ends, said method further comprising first and second steps of splicing said first and second ends, respectively, into said pump line using first and second vacuum connections.

11. A method as in claim 10, wherein each of said steps of splicing said first and second ends into said pump line, comprises the steps of:
   providing first and second flanges;
   positioning a centering ring between said first and second flanges;
   mounting an O-ring on said centering ring; and
   holding said centering ring and said first and second flanges tightly together by a clamp ring, such that said O-ring effectuates a vacuum seal at said vacuum connection.

12. A method as in claim 11, wherein said step of providing particle filter mounts said particle filter in the one of said first and second vacuum connections located further from said loadlock chamber.

* * * * *